United States Patent [19]
Cameron

[11] Patent Number: 5,594,287
[45] Date of Patent: Jan. 14, 1997

[54] HIGH VOLTAGE SOLID STATE RELAY

[75] Inventor: David B. Cameron, McMinnville, Oreg.

[73] Assignee: Hewlett-Packard Company, Palo Alto, Calif.

[21] Appl. No.: 334,469

[22] Filed: Nov. 4, 1994

Related U.S. Application Data

[62] Division of Ser. No. 79,115, Jun. 17, 1993, Pat. No. 5,395,394.

[51] Int. Cl.⁶ .................................................. H01H 47/00
[52] U.S. Cl. .................................................. 307/132 E
[58] Field of Search ................................. 327/436, 437; 307/132 E

[56] References Cited

U.S. PATENT DOCUMENTS

| | | | |
|---|---|---|---|
| 3,782,389 | 1/1974 | Bell | 128/419 D |
| 3,862,636 | 1/1975 | Bell et al. | 128/419 D |
| 4,566,457 | 1/1986 | Stemple | 128/419 D |
| 4,594,632 | 6/1986 | Unnewehr | 361/33 |
| 4,754,176 | 6/1988 | Jones et al. | 307/571 |
| 4,873,470 | 10/1989 | Myers | 315/240 |
| 5,097,830 | 3/1992 | Eikefjord et al. | 128/419 D |
| 5,163,427 | 11/1992 | Keimel | 128/419 D |
| 5,222,492 | 6/1993 | Morgan et al. | 128/419 D |
| 5,285,779 | 2/1994 | Cameron et al. | 607/5 |

FOREIGN PATENT DOCUMENTS

| | | | |
|---|---|---|---|
| 0246064 | 11/1987 | European Pat. Off. | A61N 1/39 |
| 0326290 | 8/1989 | European Pat. Off. | A61N 1/38 |
| 0546666 | 6/1993 | European Pat. Off. | A61N 1/39 |

*Primary Examiner*—William M. Shoop, Jr.
*Assistant Examiner*—Kim Lockett
*Attorney, Agent, or Firm*—Curtis G. Rose

[57] ABSTRACT

A solid state relay, suitable for use in a defibrillator or other high voltage application, is disclosed. Upon activation by a switch, the solid state relay switches power from a high voltage power source, such as a capacitor, to a load, such as a patient undergoing defibrillation. The solid state relay has a group of at least two relay sections that share the voltage load such that no one relay section experiences an overvoltage condition due to the parametric variations of each relay section. Each relay section contains a subsection responsible for balancing the off-state voltage between the relay sections, a subsection responsible for controlling the change of voltage over time as the switch is activated, and a subsection for controlling the change of voltage over time as the switch is deactivated. The solid state relay also contains an output section responsible for minimizing the leakage current from the relay group to the load. The switch is optically coupled to the relay group to provide an isolation boundary.

11 Claims, 9 Drawing Sheets

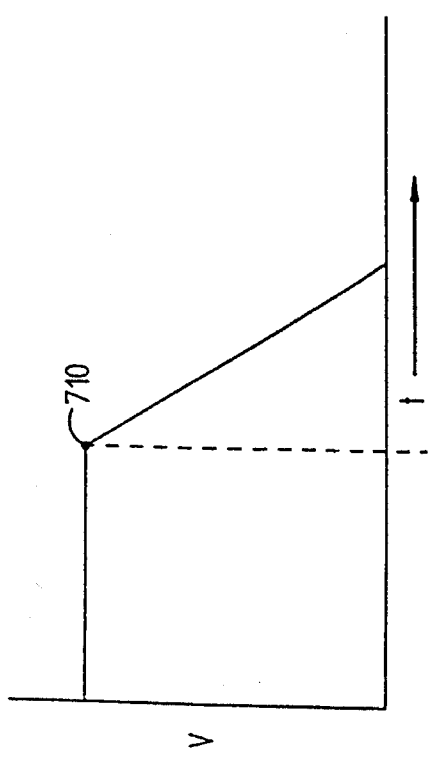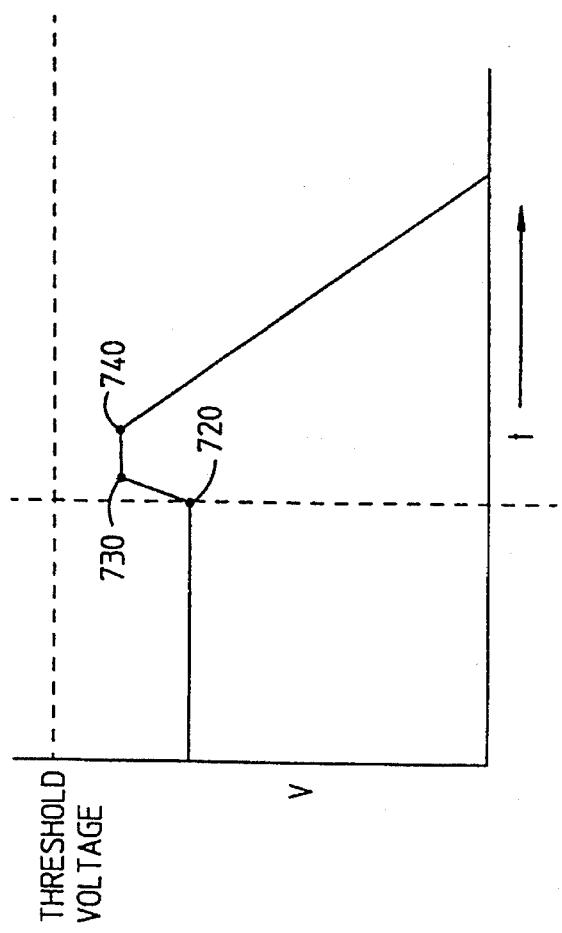

5,594,287

HIGH VOLTAGE SOLID STATE RELAY

CROSS REFERENCE TO RELATED APPLICATION(s)

This is a divisional of application Ser. No. 08/079,115 filed on Jun. 17, 1993 now U.S. Pat. No. 5,395,394.

FIELD OF THE INVENTION

This invention relates to the electronics circuitry field. More particularly, this invention is a solid state relay suitable for a wide variety of high voltage applications, such as a defibrillator.

BACKGROUND OF THE INVENTION

Mechanical relays have been used for years to switch high voltages from a source to a load. For example, defibrillators have relied on mechanical relays to transfer energy stored in a high voltage capacitor, via defibrillation paddles, to a patient undergoing defibrillation. While mechanical relays are the stalwart of such applications, they are not without their problems. For example, mechanical relays are, by modern standards, notoriously slow to switch. In addition, mechanical relays require high coil switching currents to achieve switching times, are subject to wearout, can be damaged or destroyed by load interruption, and can inadvertently discharge or be damaged by environmental mechanical shock (i.e. being bumped or dropped). If this weren't enough, mechanical relays are also large and very costly, and can cause sparks that could be unpleasant, to say the least, in combustible environments.

Solid state relays are known in the art, but these relays are unsuitable in high voltage applications where voltages exceeding the limit of the device (currently around 1200 volts) are required to be switched. Failure, perhaps spectacular in nature, would be the result if such a prior art relay were to be placed in a defibrillator, where voltages in excess of 5,000 volts are required to be switched. U.S. Pat. No. 4,754,176 discloses a high voltage solid state relay that might be suitable for some applications, but has inherent problems of its own that makes this attempt wholly unsatisfactory for many other applications, including a defibrillator. For example, the solid state relay disclosed in this patent performs its switching operation so fast that it is susceptible to inadvertent triggering. While inadvertent triggering may be tolerable in some applications, it is clearly undesirable in most applications, and can be intolerable or even fatal in other applications, such as defibrillators, or elsewhere where human beings may be on the receiving end of a high voltage relay that has been inadvertently triggered.

In addition, the relay disclosed in the above patent requires a very complex and expensive transformer for operation, and does not disclose any mechanism of preventing the individual components of the relay from experiencing an overvoltage condition, due to the tolerances and other physical attributes of the components in the relay, that has the potential of destroying the component.

SUMMARY OF THE INVENTION

It is a primary object of the invention to provide an enhanced solid state relay.

It is another object of the invention to provide a solid state relay suitable for a wide variety of high voltage applications.

It is another object of the invention to provide a solid state relay suitable for use in a defibrillator.

It is another object of the invention to provide a solid state relay that is not susceptible to inadvertent triggering.

It is another object of the invention to provide a solid state relay that is not susceptible to overvoltage conditions.

These and other objects are accomplished by the high voltage solid state relay disclosed herein.

A solid state relay, suitable for use in a defibrillator or other high voltage application, is disclosed. Upon activation by a switch, the solid state relay switches power from a high voltage power source, such as a capacitor, to a load, such as a patient undergoing defibrillation. The solid state relay has a group of at least two relay sections that share the voltage load such that no one relay section experiences an overvoltage condition due to the parametric variations of the components of each relay section. Each relay section contains a subsection responsible for balancing the off-state voltage between the relay sections, a subsection responsible for controlling the change of voltage over time as the switch is activated, and a subsection for controlling the change of voltage over time as the switch is deactivated. The solid state relay also contains an output section responsible for minimizing the leakage current from the relay group to the load. The switch is optically coupled to the relay group to provide an isolation boundary.

DESCRIPTION OF THE DRAWINGS

FIGS. 7A–7B show the voltage waveform of a typical and a slow relay section as the switch is activated.

DETAILED DESCRIPTION OF THE PREFERRED EMBODIMENT

Figure 1:
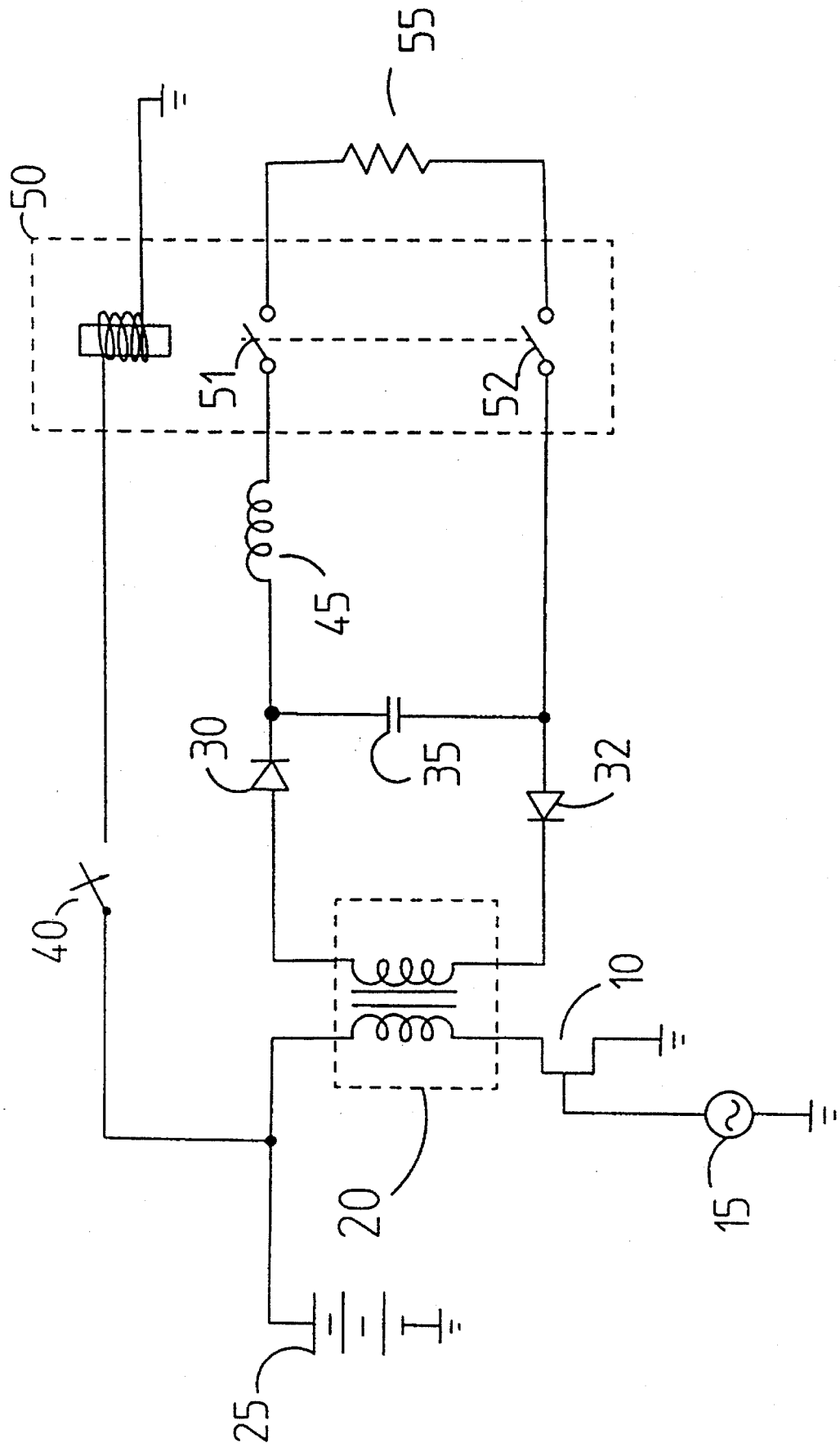
FIG. 1 shows the basic components of a conventional defibrillator circuit.

FIG. 1 shows the basic components of a conventional defibrillator circuit. Transistor 10 is switched by oscillator 15 to generate an AC current in the primary of transformer 20 from the power supplied by battery 25. This induces an AC current in the secondary of transformer 20. This current is rectified by diodes 30 and 32, and charges high voltage capacitor 35. When switch 40 is closed by the operator (or through other means, such as automatically), mechanical relay 50 is energized (i.e. relay poles 51 and 52 close), thereby delivering the charge on capacitor 35 to the patient under defibrillation, represented by resistor 55. Inductor 45 provides waveshaping of the current pulse provided to the patient. Diode 32 and relay pole 52 keep the circuit balanced around ground, thereby addressing the parasitic effects of the circuit.

Figure 2:
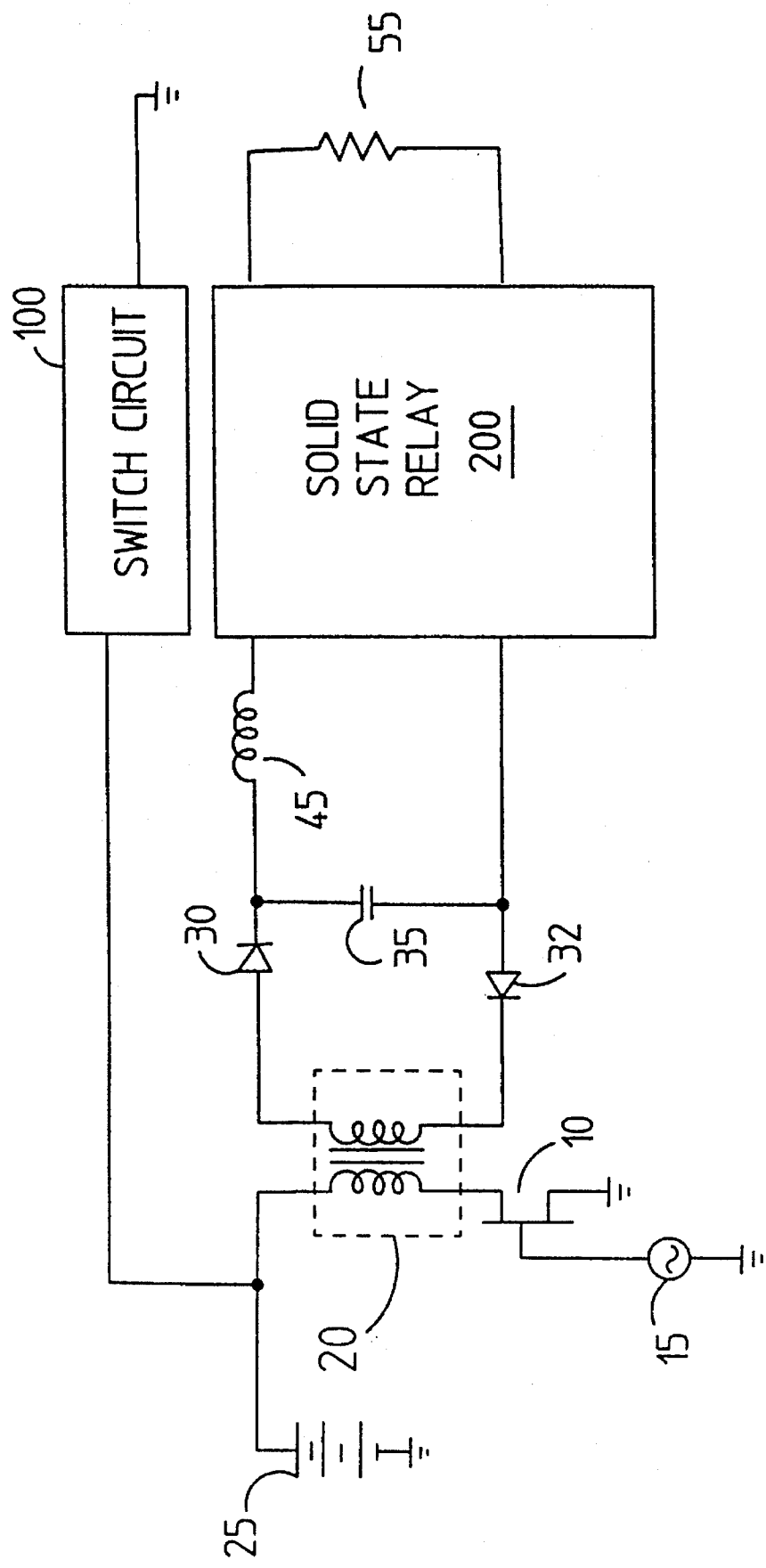
FIG. 2 shows a defibrillator circuit incorporating the solid state relay of the invention.

FIG. 2 shows a defibrillator circuit incorporating the solid state relay of the invention. Those skilled in the art will notice that many components of the circuit of FIG. 2 are the same as the components of the circuit of FIG. 1, as identified by like reference numerals. Switch 40 of FIG. 1 has been replaced by switch circuit 100, which will be explained in more detail later. Mechanical relay 50 has been replaced by solid state relay 200, which will also be explained in more detail later.

Figure 3:
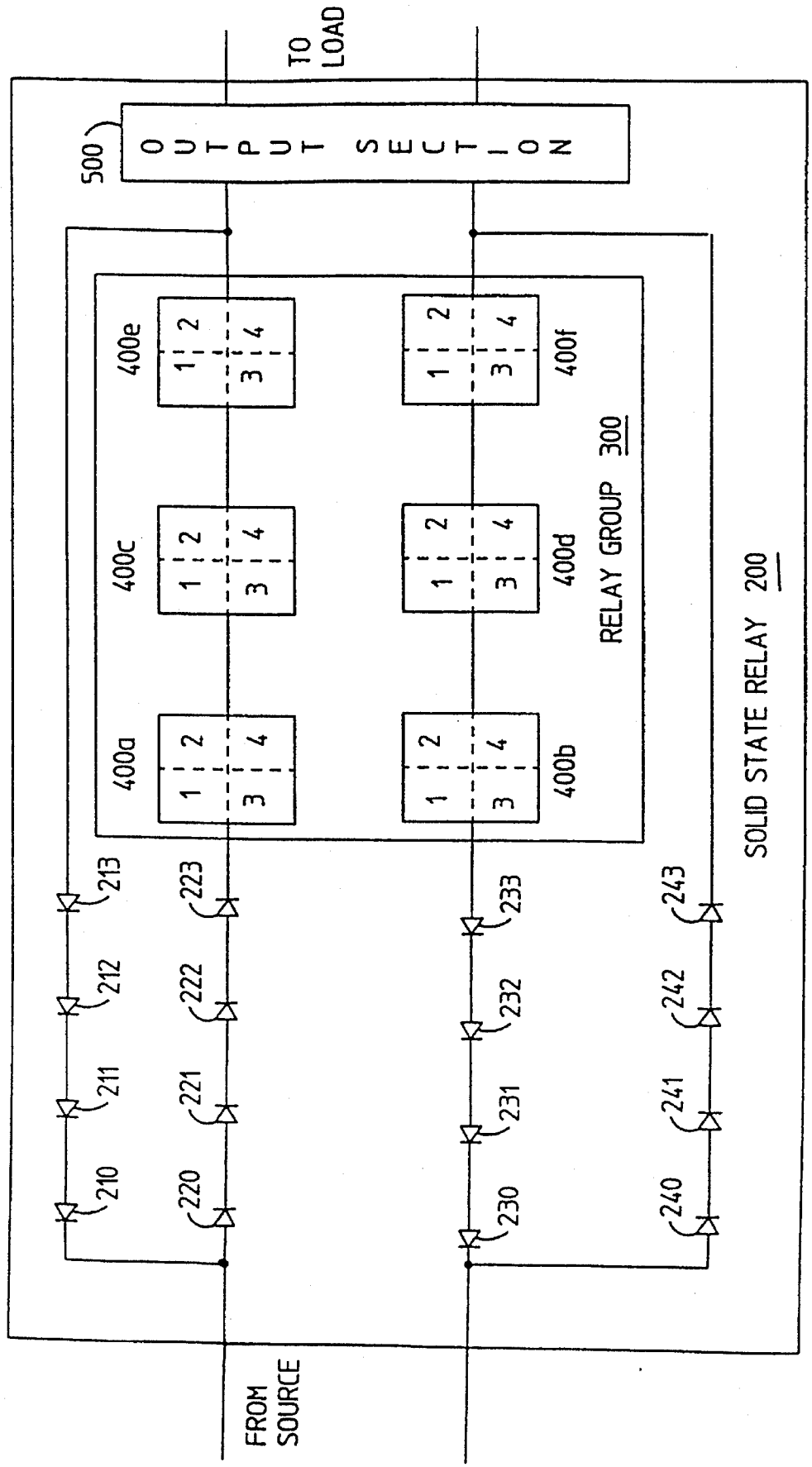
FIG. 3 shows a block diagram of the solid state relay of the preferred embodiment of the invention.

FIG. 3 shows a block diagram of solid state relay 200 of the preferred embodiment of the invention. Relay 200 contains diodes 210–213, 220–223, 230–233, and 240–243, relay group 300, and output section 500. Relay group 300 contains relay sections 400a–400f. Each relay section 400 is divided up into relay subsections 400-1–400-4. In the preferred embodiment, these subsections correspond to various functions performed by relay section 400, primarily to prevent an overvoltage condition due to the parametric variations of the relay sections in relay group 300. The use of the term "parametric variations" herein shall mean the difference in the theoretical operation and the actual operation of the relay sections in relay group 300, due to variances in specified tolerances or other unspecified electronic properties in the components contained in the relay sections. For example, a resistor having a theoretical value of 100 ohms may actually have a measured value of 97 ohms. In addition, the gate capacitance can vary from one transistor to another, even though this electronic property of a transistor is often unspecified. These parametric variations can result in relay sections which switch too fast or too slow relative to the other relay sections, or are otherwise not balanced with the other relay sections, resulting in one or more relay sections experiencing a potentially disastrous overvoltage condition.

While six relay sections and four relay subsections are shown in FIG. 3, those skilled in the art will appreciate that anywhere from two to perhaps dozens, hundreds, or even thousands of relay sections can be contained in relay group 300, and anywhere from one to dozens of subsections can be contained in relay section 400, and still fall within the spirit and scope of the invention.

Diodes 210–213, 220–223, 230–233, and 240–243 protect relay group 300 from spurious turn on or damage due to electrostatic discharge events. Diodes 210–213 and 240–243 conduct current during periods of undershoot caused by switching an underdamped load. Diodes 220–223 and 230–233 are normally forward biased, but will become reversed biased during an electrostatic discharge event, during which time diodes 210–213 (large positive electrostatic voltage) or 240–243 (large negative electrostatic voltage) may become forward biased.

Figure 4:
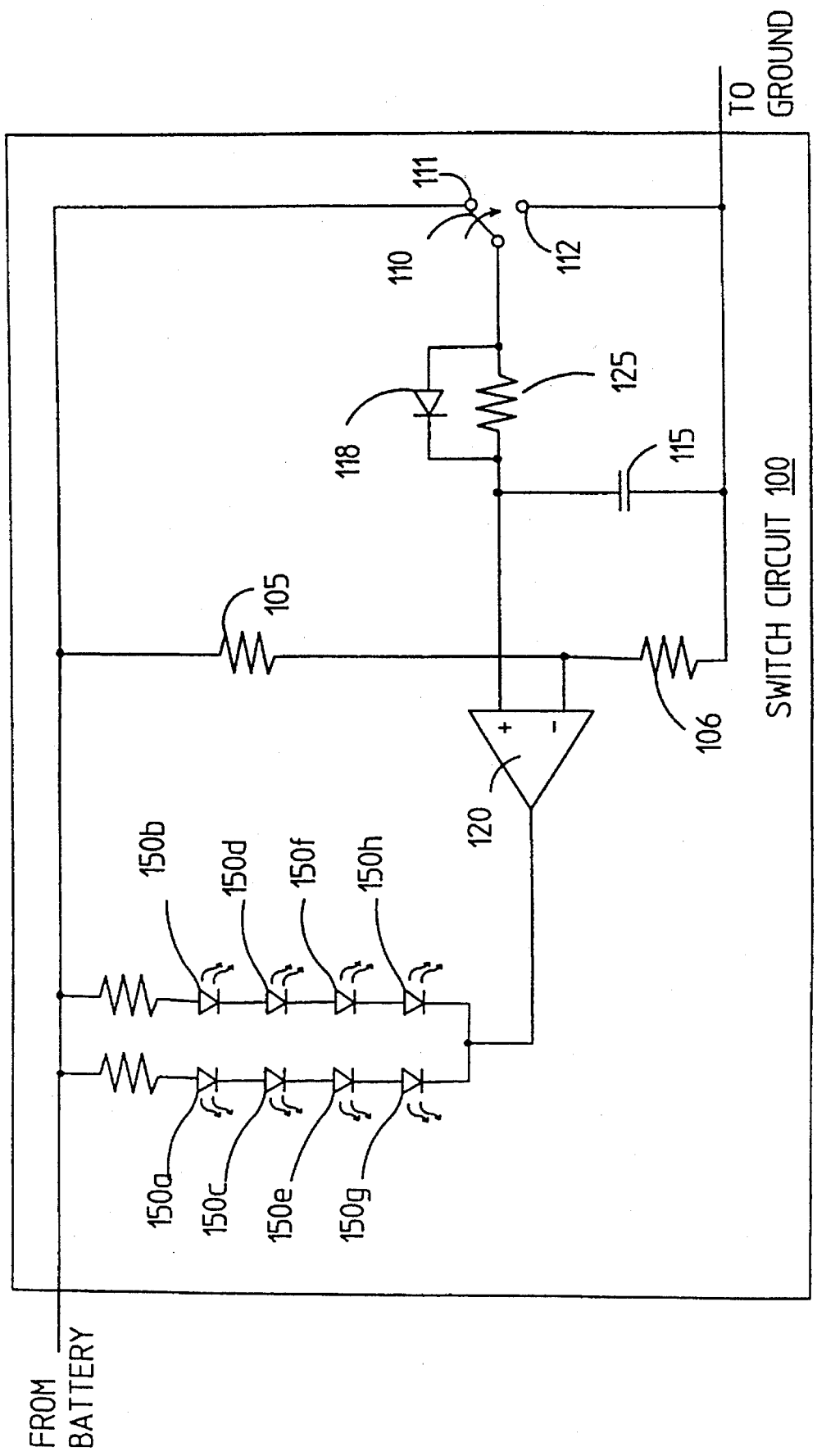
FIG. 4 shows a schematic of the switch circuit of the invention.

FIG. 4 shows a schematic of switch circuit 100 of the invention. The resistor divider formed by resistors 105 and 106 set a reference voltage at the negative input of comparator 120. This reference is between the battery voltage and ground. With switch 110 in position 111, capacitor 115 is charged to the voltage level of battery 25 (FIG. 2) through diode 118. The voltage at the positive terminal of comparator 120 is therefore higher than the voltage at the negative terminal, thereby making the output of comparator 120 high. When the output of comparator 120 is high, no current can flow through light emitting diodes 150, thus turning them off. When switch 110 is moved to position 112, capacitor 115 begins to discharge through resistor 125. When the voltage across capacitor 115 drops below the voltage across the resistor divider 105 and 106, comparator 120 switches to a low state, thus turning light emitting diodes 150 on. Switch circuit 100 prevents "bounce" or noise from switch 110 from inadvertently triggering light emitting diodes 150.

In the preferred embodiment, light emitting diodes 150a–150f physically reside in optocoupler 425 (FIG. 5) of each of the six relay sections 400a–400f, respectively. Likewise, light emitting diodes 150g and 150h physically reside in optocouplers 525 and 555 (FIG. 6) of output section 500. Those skilled in the art will appreciate that the optocouplers of FIGS. 5 and 6 could be replaced with photodetectors that receive signals from a single light source transmitted via light pipe, fiber optic cable, etc, and still fall within the spirit and scope of the invention.

Figure 5:
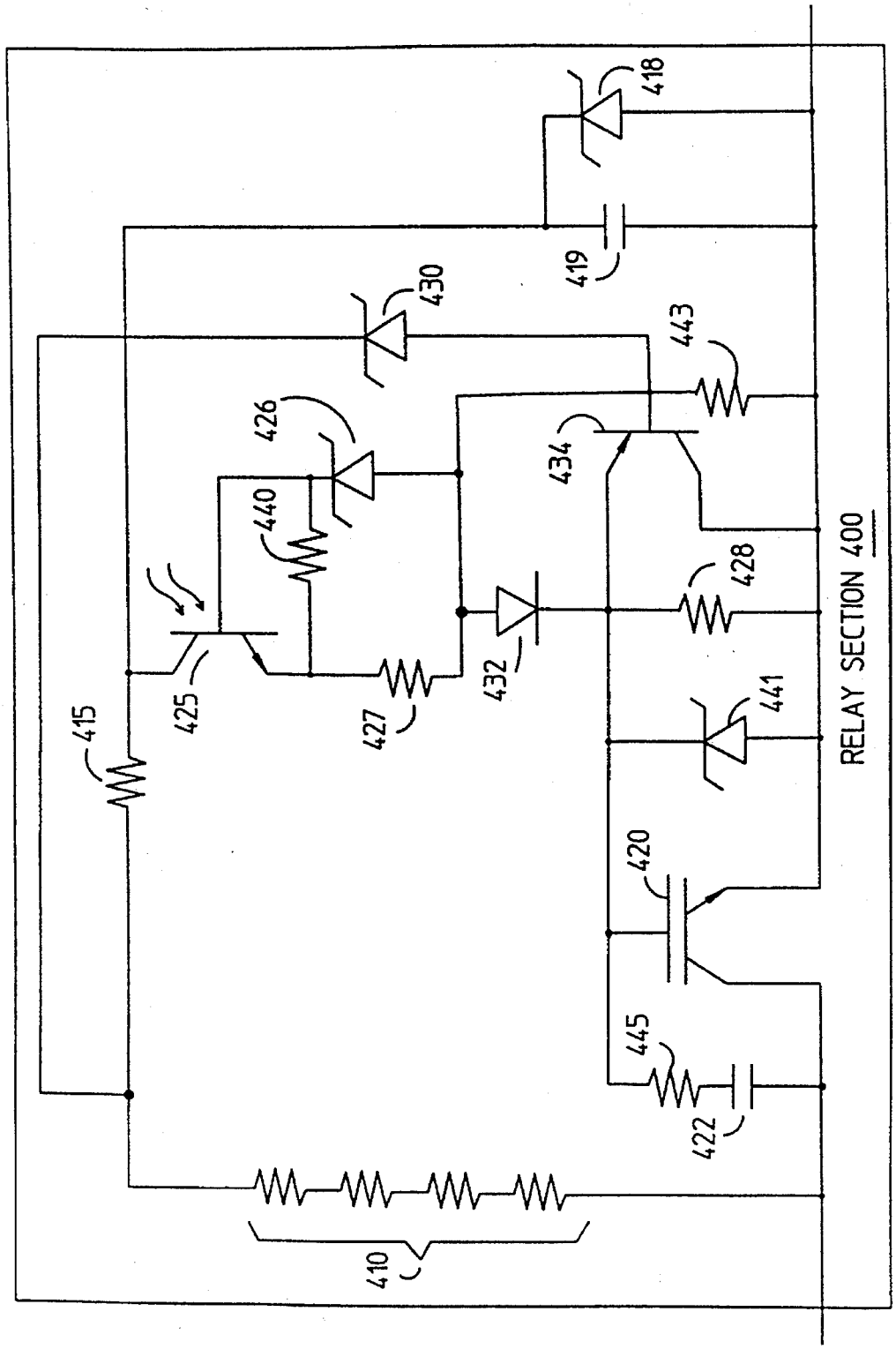
FIG. 5 shows a schematic of a relay section of the invention.

FIG. 5 shows a schematic of relay section 400 of the invention. The use of reference numerals 400a–400f in relay group 300 is used to indicate that each relay section 400a–400f contains identical circuitry 400, as shown in more detail in FIG. 5.

In the preferred embodiment, relay section 400 of FIG. 5 is logically segmented into subsections, as shown in FIG. 3. As previously discussed, these subsections correspond to various functions performed by relay section 400, primarily to prevent an overvoltage condition due to the parametric variations of the components in the relay sections of relay group 300. These subsections include a subsection responsible for balancing the off-state voltage between the relay sections, a subsection responsible for controlling the change of voltage over time as the switch is activated, and a subsection for controlling the change of voltage over time as the switch is deactivated.

Note that the components for particular subsections of relay section 400 are not necessarily physically grouped together. In addition, some components are used in more than one subsection.

The operation of each subsection of relay section 400 of FIG. 5 will now be described in more detail. Relay subsection 400 1 is responsible for balancing the off-state voltage between relay sections. In the preferred embodiment, this occurs during the period where high voltage capacitor 35 (FIG. 2) is being charged, while the charge on capacitor 35 is being held prior to discharge, and in the event energy is bled off capacitor 35 during a disarm or energy turn-down operation. Resistors 410, resistor 415, and zener diode 418 of each relay section 400, in addition to resistor 510 and zener diodes 515–517 of output section 500 (FIG. 6), form a voltage divider across high voltage capacitor 35 during these periods. Since transistor 420 of each relay section 400 does not conduct during these periods, the voltage across each relay section 400 is set by the series current flow through the divider network of resistors 410, resistor 415, and zener diode 418. In the preferred embodiment, resisters 410 are shown as a plurality of lower voltage resistors so that small, surface mount resistors can be used. If output section is not present, as is the case with an alternate embodiment which will be discussed later (FIG. 9), load 55 becomes an element in the voltage divider network.

Relay subsection 400-2 is responsible for controlling the change of voltage over time as switch 110 is activated. Because the components of each relay section have parametric variations that cause the relay sections to turn on at slightly different rates relative to other relay sections in response to the activation of switch 110, it is likely that some of the relay sections will turn on faster than others, leaving the relay sections that are slower to turn on holding off more, or all, of the voltage. When this occurs, an overvoltage condition can develop across the transistors in the relay sections. This overvoltage condition, unless controlled, can result in the destruction of the transistors and/or other components in the relay sections.

To control this overvoltage condition, capacitor 422 provides a feedback path to the gate of transistor 420. When the light emitting diode 150 inside optocoupler 425 is energized, optocoupler 425 turns on. AS optocoupler 425 turns on, it, in combination with zener diode 426 and resister 427, forms a current source supplying the gate of transistor 420. As transistor 420 starts to turn on, the collector-emitter voltage across transistor 420 begins to drop, causing the voltage across capacitor 422 to drop. This induces a current out of the gate of transistor 420 through capacitor 422 given by the relation I=C*dv/dt. This current tends to try and turn transistor 420 off at the same time that optocoupler 425 is trying to turn it on. The net result is that these two currents balance and the slew rate of the collector-emitter voltage of transistor 420 is given by dv/dt=C/I, where I is the current from the current source from optocoupler 425, zener diode 426 and resistor 427, and where C is the capacitance of capacitor 422.

In order to illustrate the operation of subsection 400-2 of relay section 400, assume that relay group 300 contains two relay sections: 400a and 400b, and that relay section 400b is slower to turn on than relay section 400a. FIG. 7A shows the change of voltage over time for "typical" relay section 400a, and FIG. 7B shows the change of voltage over time for "slow" relay section 400b (both measurements taken across the collector-emitter junction of transistor 420). When relay section 400a starts to turn on (point 710 in FIG. 7A), it experiences a negative dv/dt. As this occurs, slower relay section 400b starts to experience a positive dv/dt (point 720, FIG. 7B), since the total voltage across the two relay sections is constant. The jump in voltage from point 720 to point 730 is equal to the gate voltage of transistor 420 times the gate capacitance of transistor 420, divided by the capacitance of capacitor 422. Therefore, it is important to select a relatively large capacitance value for capacitor 422 to keep the voltage step between points 720 and 730 reasonably small. The steepness of the slope of the voltage step between points 720 and 730 is proportional to the number of relay sections in relay group 300 (i.e. the more relay sections, the steeper the slope).

The positive dv/dt across transistor 420 of relay section 400b causes a current to be induced in capacitor 422 of relay section 400b, but in the opposite direction from the current induced in capacitor 422 of relay section 400a, discussed above. In other words, the current induced in capacitor 422 of relay section 400b is into the gate of transistor 420. This current has the tendency to turn transistor 420 on. However, in order to maintain this current, the dv/dt must stay positive, so the voltage across relay section 400b must continue to increase. By causing the current flow out of the gate (through resistor 428) to be very low, the balancing current into the gate (I=C*dv/dt) is also very low, and dv/dt is therefore held to a very small value. This is shown between points 730 and 740 in FIG. 7B (although the slope is so small it appears to be almost flat between these two points). Therefore, a fairly long time delay (dt) results in a fairly small voltage increase (dv). This delay means it takes transistor 420 a relatively long time to reach its threshold voltage. Before transistor 420 ever reaches its threshold voltage, optocoupler 425 (even if very slow) will have turned on, thereby turning on transistor 420 (as shown at point 740 in FIG. 7B).

Relay subsection 400-3 is responsible for controlling the change of voltage over time as switch 110 is deactivated. Similar to the case discussed above when switch 110 is activated, each relay section 400 can turn off at a slightly different time or rate, and any remaining voltage on capacitor 35 (FIG. 2) may not be equally shared across relay sections, and an overvoltage condition can result. While similar to the case discussed above, this situation is actually harder to control, since there is no fixed upper limit to the voltage to control against, and controlling the slew rate does not guarantee that a relay section will not experience an overvoltage condition. In the preferred embodiment, where the solid state relay is used in a defibrillator, the worst case scenario is where the defibrillator paddles are open (i.e. not in contact with a low resistive patient) and discharge at full energy. This worst case scenario is handled by zener diode 430, in conjunction with resistors 410 and resistor 415.

These components cause the voltage across transistor 420 to have a stepped slew rate as switch 110 is disabled. The slew rate is allowed to be very high until the voltage across the voltage divider created by resisters 410 and resistor 415 becomes high enough to start to turn on zener diode 430. As zener diode 430 reverse biases and starts to conduct, the slew rate across transistor 420 will drop dramatically. This is due to the conduction of current through zener diode 430 and diode 432 into the gate of transistor 420. This turns off transistor 434, and tends to turn on transistor 420.

Figure 8A:
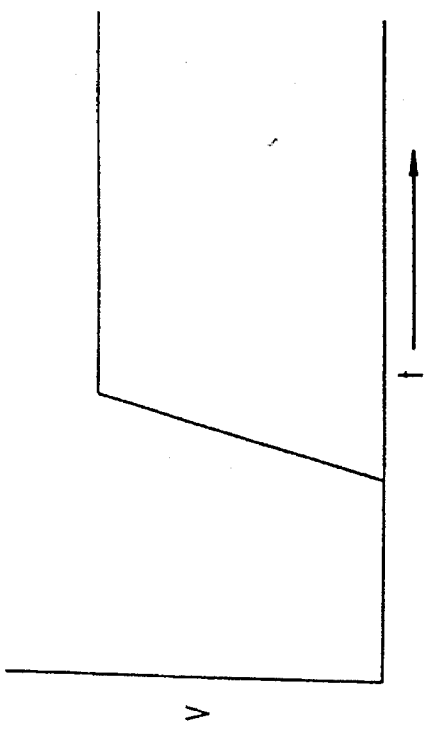
FIGS. 8A–8B show the voltage waveform of a typical and a fast relay section as the switch is deactivated.
Figure 8B:
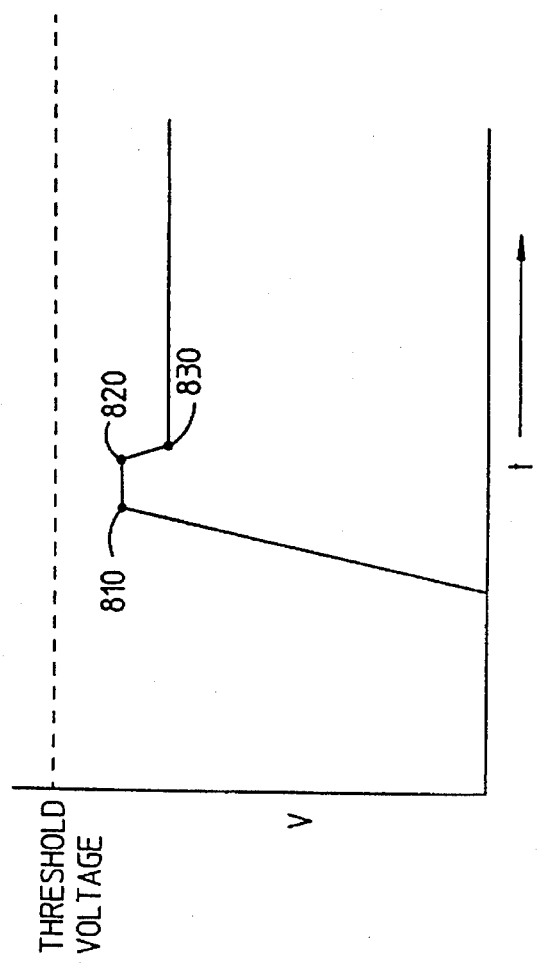

In order to illustrate the operation of subsection 400-3 of relay section 400, assume that relay group 300 contains two relay sections: 400a and 400b, and that relay section 400b is faster to turn off than relay section 400a. FIG. 8A shows the change of voltage over time for "typical" relay section 400a, and FIG. 8B shows the change of voltage over time for "fast" relay section 400b (both measurements taken across the collector-emitter junction of transistor 420). A "fast" relay section would normally experience an overvoltage condition, because its voltage is slewing faster than the others. As its voltage reaches the point where zener diode 430 turns on, however, it is clamped by zener diode 430, thereby giving the slower relay states a chance to catch up. At point 820 of FIG. 8B, "typical" relay section 400a has caught up and turned off, and is now taking on its fair share of the voltage. As this happens, the slope on "fast" relay section 400c reverses direction towards its steady state-off voltage level, reached at point 830.

Relay subsection 400-4 is responsible for performing several "miscellaneous" functions of relay section 400. Relay subsection 400-4, through the use of resistor 440, is responsible for decreasing the sensitivity of optocoupler 425 to leakage capacitance and dv/dt across the isolation boundary between optocoupler 425 and switch circuit 100. In addition, relay subsection 400-4, through the use of zener diode 418 and capacitor 419, form a power supply to power the turn on circuit while the voltage across transistor 420 is low due to the relay section being turned on. The function of the remaining components in relay subsection 400-4 will now be discussed. Zener diode 441 helps protect the gate of transistor 420 from overvoltage. Resistor 443 provides a bias current path which causes transistor 434 to turn on when optocoupler 425 is off. Resistor 445 limits the current that can be conducted through capacitor 422, thus causing transistor 420 to be less sensitive to small dv/dt changes when transistor 420 is turned on and its collector to emitter voltage is low.

Figure 6:
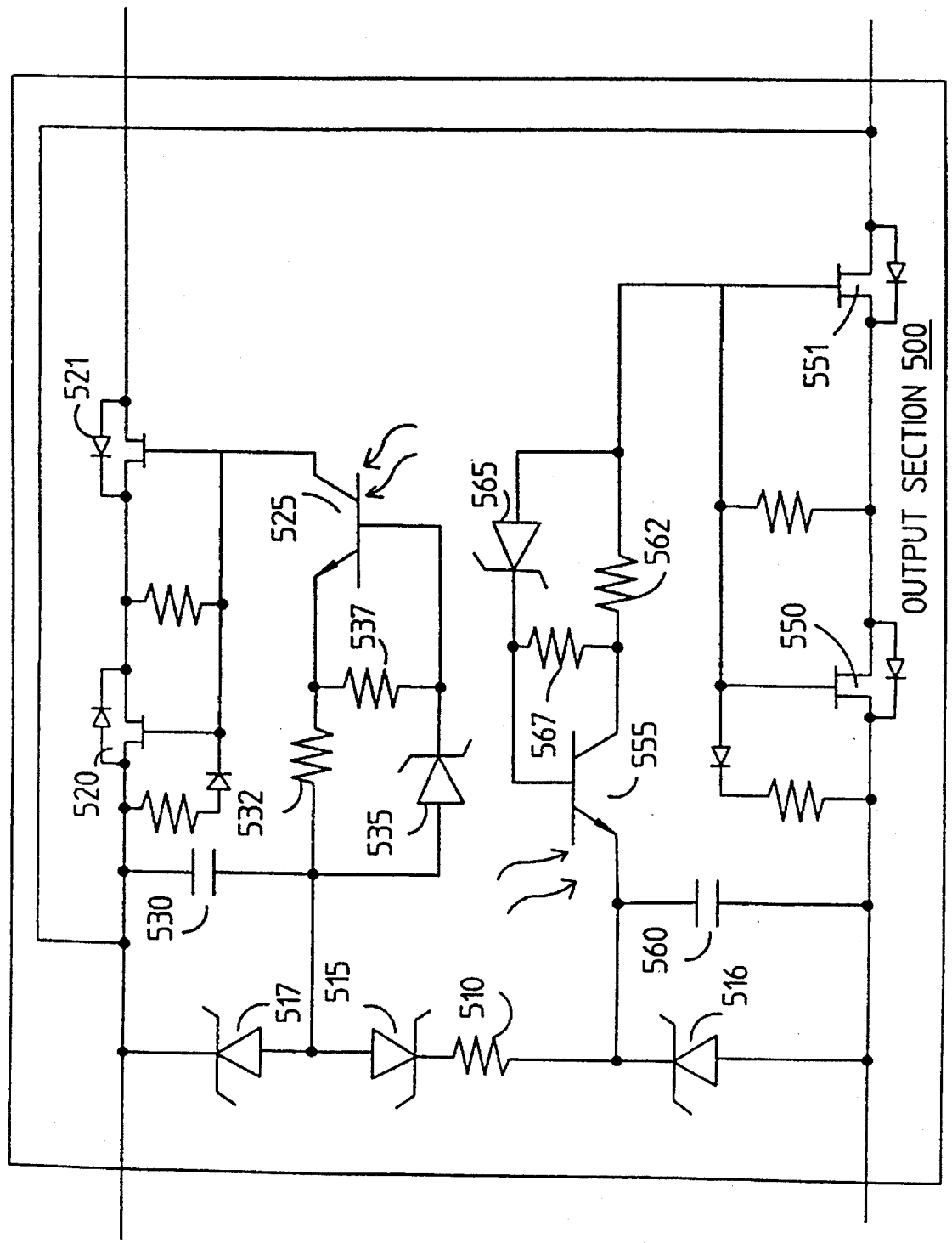
FIG. 6 shows a schematic of the output section of the invention.

FIG. 6 Shows a schematic of the output section of the invention. As mentioned previously, limiting the leakage current to the load is important in many applications, such as the defibrillator of the preferred embodiment. In the preferred embodiment, transistors 520 and 521 are low voltage, high current P-Channel MOSFETS. The sources of these two transistors are connected together, and are turned on by the current source formed by optocoupler 525 and the combination of zener diode 517, capacitor 530, resistor 532, zener diode 535, and resistor 537. These transistors are only turned on when optocoupler 525 turns on, in response to having its light emitting diode 150 energized (FIG. 4). Operation of this circuit is similar to the operation of relay subsection 400-2 discussed above. Similarly, transistors 550 and 55 1 are low voltage, high current N-Channel MOSFETS. The sources of these two transistors are connected together, and are turned on by the current source formed by optocoupler 555 and the combination of zener diode 516, capacitor 560, resistor 562, zener diode 565, and resistor 567. Resistor 510 completes the off-state bias current path, and is large enough to withstand the on-state voltage that is impressed across it. In addition zener diodes 516 and 517 must be able to withstand fairly high reverse current pulses through the on-state. Zener diode 515 prevents discharge of capacitors 530 and 560 in the event that the output voltage of output section 500 slews negative due to ringing in an underdamped load. When transistors 520, 521, 550, and 551 are off, the leakage current between output section 500 and load 55 (FIG. 2) is very low. In the preferred embodiment, leakage currents in the order of tens of picoamps is typical.

Figure 9:
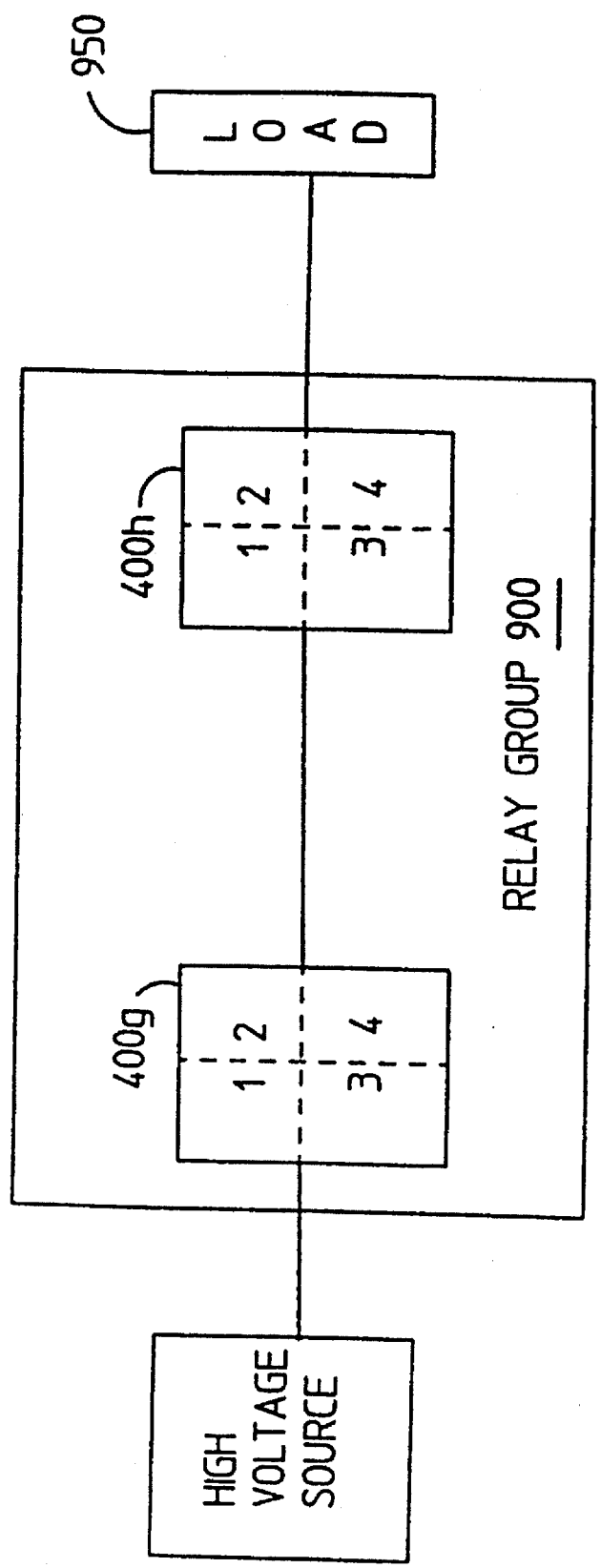
FIG. 9 shows a block diagram of the solid state relay of an alternate embodiment of the invention.

An alternative embodiment has been contemplated, and is shown in FIG. 9. In this alternate embodiment, relay group 900 only contains two relay sections: 400g and 400h. Note that relay sections 400g and 400h contain the same circuitry of relay section 400 discussed above and shown in FIG. 5. Relay group 900 is connected to high voltage source 920 and to load 950. Note that output section 500 (FIG. 3) is not needed in this embodiment, since load 950 is not as susceptible to leakage currents as the patient undergoing defibrillation was in the preferred embodiment. In addition, diodes 210–213, 220–223, 231–234, and 241–245 (FIG. 3) are also not required, since electrostatic discharge events can be tolerated in this alternate embodiment.

Another alternate embodiment has been contemplated, where relay section 400h is modified to remove the function of one or more of the relay subsections of the invention. If this is done, it would be possible to have circuitry in only one relay section that prevents both relay sections from overvoltage conditions due to parametric variations. In this alternate embodiment, it is important for modified relay section 400h to always turn on faster than relay section 400a, and to always turn off slower than relay section 400a. To accomplish these results, relay section 400h is modified by eliminating capacitor 422. This modification assures that modified relay section 400h will always turn on faster than relay section 400a. In addition, relay section 400h is modified to eliminate transistor 434. This modification assures that modified relay section 400h will always turn off slower than relay section 400a. Of course, those skilled in the art will appreciate that other modifications could be made to relay section 400h to accomplish some or all of these results, and that similar modifications could be made to one or more relay sections where more than two relay sections are included in relay group 900.

While this invention has been described with respect to the preferred embodiment and several alternate embodiments, it will be understood by those skilled in the art that various changes in detail may be made therein without departing from the spirit, scope and teaching of the invention. For example, the circuits shown in the drawings could be replaced by other equivalent circuit structures. These equivalent circuit structures could be contained in one chip, or in a few chips. Accordingly, the herein disclosed is to be limited only as specified in the following claims.

What is claimed is:

1. A high voltage solid state relay, comprising:
   a first relay section responsive to a switch and having an input for a high voltage source;
   a second relay section responsive to said switch, connected to said first relay section, and having an output for a load; and
   circuitry in at least one of said relay sections for preventing an overvoltage condition due to parametric variations.

2. A high voltage solid state relay, comprising:
   a relay group having a plurality of relay sections, said relay group responsive to a switch, having an input connected to a high voltage source, and having an output connected to a load; and
   circuitry in at least one relay section of said relay group for preventing an overvoltage condition due to parametric variations.

3. A high voltage solid state relay, comprising:
   a relay group having a plurality of relay sections, said relay group responsive to a switch, having an input connected to a high voltage source, and having an output connected to a load;
   circuitry in at least one relay section of said relay group for preventing an overvoltage condition due to parametric variations; and
   an output section, connected to said relay group, comprising circuitry for minimizing the leakage current from said relay group to said load.

4. The high voltage solid state relay of claim 3, wherein said switch is optically coupled to said relay group.

5. A high voltage solid state relay, comprising:
   a relay group having a plurality of relay sections, said relay group responsive to a switch, having an input connected to a high voltage source, and having an output connected to a load;
   circuitry in at least one relay section of said relay group for preventing an overvoltage condition due to parametric variations; said circuitry further comprising: a first subsection for balancing the off-state voltage between relay sections in said group of relay sections.

6. The high voltage solid state relay of claim 5, wherein said circuitry further comprises:
   a second subsection for controlling the change of voltage over time in each relay section of said group of relay sections as said switch is activated.

7. The high voltage solid state relay of claim 6, wherein said circuitry further comprises:
   a third subsection for controlling the change of voltage over time in each relay section of said group of relay sections as said switch is deactivated.

8. A high voltage solid state relay, comprising:
   a first relay section responsive to a switch and having an input for a high voltage source;
   a second relay section responsive to said switch and connected to said first relay section, and having an output for a load; and
   circuitry in at least one of said relay sections for preventing an overvoltage condition due to parametric variations, said circuitry further comprising:
   a first subsection for balancing the off-state voltage between said first relay section and said second relay section.

9. The high voltage solid state relay of claim 8, wherein said switch is optically coupled to said first relay section and to said second relay section.

10. The high voltage solid state relay of claim 8, wherein said circuitry further comprises:
    a second subsection for controlling the change of voltage over time as said switch is activated.

11. The high voltage solid state relay of claim 10, wherein said circuitry further comprises:
    a third subsection for controlling the change of voltage over time as said switch is deactivated.

* * * * *